United States Patent [19]
Crosby, Jr.

[11] 3,956,631
[45] May 11, 1976

[54] PROCESS FOR NON-DESTRUCTIVE INSPECTION

[75] Inventor: Edward Lewis Crosby, Jr., Indialantic, Fla.

[73] Assignee: RCA Corporation, New York, N.Y.

[22] Filed: June 20, 1974

[21] Appl. No.: 481,207

[52] U.S. Cl. .............................. 250/321; 250/323; 250/358 R
[51] Int. Cl.² ........................................ G03B 41/16
[58] Field of Search ........... 250/321, 323, 358, 359, 250/360, 308

[56] References Cited
UNITED STATES PATENTS
3,351,760   11/1967   Brown .............................. 250/321 X Primary Examiner—Archie R. Borchelt
Attorney, Agent, or Firm—Edward J. Norton; William Squire

[57] ABSTRACT

A process for non-destructive inspection of a fusion bonded laminated article comprises disposing a pattern of material on a fusible adhesive layer disposed between two layers of the article. The layers and adhesive are fused together wherein the fusing causes a distortion in the pattern. The article is examined for the presence of the distortion which presence manifests an acceptable bonded joint.

10 Claims, 7 Drawing Figures

PROCESS FOR NON-DESTRUCTIVE INSPECTION

This invention was made in the course of or under a contract or subcontract thereunder with the Department of the Air Force.

BACKGROUND OF THE INVENTION

1. Field of Invention

The present invention relates to the nondestructive inspection of fusion bonded laminated articles.

2. Description of the Prior Art

Many articles of manufacture are constructed by fusion bonding first and second layers of material together by the application of heat and pressure. This type of bonding is particularly suitable in the plastics industry in which the article material readily responds to the fusing process. A type of article particularly suited for the bonding process is one of the inflatible type such as inflated buildings and stabilized balloons as used in communications, weather stations and the like. Such articles are fabricated of layers of cloth and synthetic materials fused together at numerous seams.

The problem with such articles is that it has been extremely difficult to detect a poor or marginal seam until the article actually has been inflated and utilized for its particular purpose. A seam failure at that time may cause destruction of the article and is extremely costly.

In the manufacture of such an article, a solid adhesive is disposed between the first and second layers to be joined together. The seam is placed under heat and pressure which fuses the solid adhesive material causing it to provide a bond between the layers. The usual way for testing such a seam is to inflate the article and, if the article does in fact inflate, then it is assumed that the article is acceptable. However, the application of too little heat or too much heat may result in the seam being weak and the point for subsequent failure. The only practical way in the prior art of detecting the strength of the seam is to test to destruction by overstressing the article. However, the manufacture of one article by a given process does not necessarily guarantee that all articles will conform ideally to the requirements of the process.

SUMMARY OF THE INVENTION

A process for the non-destructive inspection of a fusion bonded laminated article comprises depositing a material in a given pattern on one layer in the interface between first and second layers of the article. The layers are bonded together by fusing the one layer at the interface. The fusing distorts the pattern. The bonded layers are then inspected for the presence of the distorted pattern. The presence of the given undistorted pattern in the bonded layers indicates lack of fusion and a poor bond.

IN THE DRAWINGS

FIG. 1 is a fragmented isometric view of an embodiment of the present invention, FIGS. 2a, 2b and 2c are various patterns useful in explaining the present invention, FIG. 3 is an isometric view illustrating a process for producing the pattern of FIG. 2a, and FIGS. 4a and 4b illustrate pattern distortions useful in explaining the present invention.

DETAILED DESCRIPTION

Figure 1:
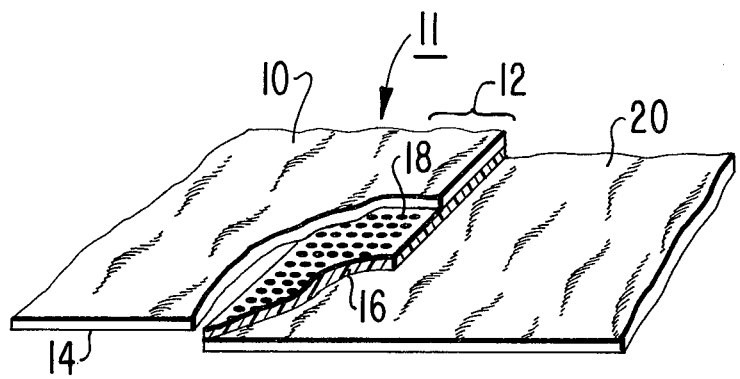

In FIG. 1, a first layer 10 of a laminated article 11 is disposed with surface 14 of edge portion 12 juxtaposed contiguous with a surface of elongated strip of solid, fusible adhesive 16. A second layer 20 of the laminated article 11 is disposed on the side of adhesive layer 16 opposite layer 10 with the adhesive 16 sandwiched between the two layers 10 and 20. In the balloon industry layers 10 and 20 are woven fabrics which are relatively transparent to electromagnetic energy. The necessity of the electromagnetic transparency of the laminae of the article will be explained later. The laminate layers 10 and 20 may comprise additional materials in accordance with a particular application of the article manufactured. As provided in accordance with the present invention, these additional materials are also relatively transparent to electromagnetic energy.

While adhesive 16 is illustrated as a separate member, it should be understood adhesive 16 may take the form of an adhesive or fusible coating formed on the side of either or both layers 10 and 20 forming article 11. Adhesive 16 preferably comprises a commerically available polyester film cement which flows on the application of heat. The bonding occurs when the liquified cement resolidifies. This type of cement has a chlorinated aliphatic ketone solvent. This type of cement is well known and no further description need be provided herein.

Figure 2A:
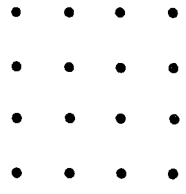

Solid fusible adhesive 16 is conveniently manufactured in thin narrow strips having a thickness preferably in the range of 2 to 10 mils. In accordance with the present invention, the strip of adhesive 16 has deposited on one side and along the entire length thereof coextensive with the laminations of article 11 a pattern 18 which is any design such as provided by a grid of dots (FIG. 2a). Pattern 18 is preferably made by depositing electromagnetic energy opaque material in dust form on the adhesive. The pattern is preferably made of barium sulfate powder or other material which is opaque to electromagnetic waves. This material should be inert with respect to the adhesive and laminae and in a fine powder dispersed in a carrier comprising the solvent for the adhesive 16. The pattern 18 is disposed or printed on one side of the adhesive 16 by any suitable means.

The laminate layers 10 and 20 and adhesive 16 are disposed in a suitable fixture (not shown) as known in the laminating art. This fixture applies heat and pressure to the laminae tending to cause the adhesive to flow and provide an adherent bond to the juxtaposed surfaces of layers 10 and 20 contiguous with the adhesive 16. One form of laminating technique is known as heat sealing and is described in Modern Plastics Encyclopedia, 1969–1970 issue, published by McGraw Hill at page 716 and in the 1968 issue at pages 1001–1005.

Upon cooling, the joint including adhesive 16, after resolidifying, is "X-rayed," preferably in the 5 to 25 kilovolt range depending on the type and thickness of the layers 10 and 20. Pattern 18 is reproduced on X-ray film since the remainder of the materials comprising layers 10 and 20 and adhesive 16 is relatively transparent to the X-ray waves. The operator examines the X-ray film in its entirety for the presence of distortion of the pattern 18. The term distortion is defined hereinafter.

A distortion of the pattern is a manifestation that the adhesive flowed during the application of heat to the lamination joints during the bonding process. When the adhesive flows, an acceptable bond is provided, while a poor bond and unacceptable joint results when the adhesive 16 fails to flow. The present invention provides a simple determination of this condition.

One characteristic of the pattern 18 is that it be sharp and finely detailed to the degree necessary to detect that fusion or flow of the adhesive 16 which is associated with an acceptable bond has occurred upon visual examination. The amount of adhesive flow corresponding to a good bond is dependent upon the viscosity and thickness of the adhesive used. The amount of flow or displacement of the adhesive is also determined by absorption characteristics of the layers to be bonded. The greater the absorption, the less the amount of flow required. The greater the thickness, the greater the amount of flow.

Figure 2B:
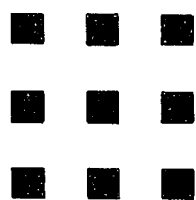
Figure 2C:
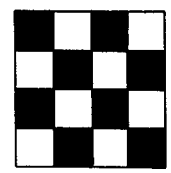

The pattern should be one that readily distorts within the range of flow present during a given set of bonding conditons including bonding temperature, layer absorptions, adhesive thickness, type and viscosity during flow. These are complex relationships which are best determined emperically for a given set of bonding conditions. To do so is within the skill of one skilled in the laminating art. Examples of typical patterns are illustrated in FIGS. 2a, 2b and 2c. FIG. 2a shows a dot pattern. This dot pattern may be made extremely fine such as occurs in a photolighographic process.

In the alternative, the pattern may be a plurality of rectangular shapes as illustrated in FIGS. 2b and 2c. In FIG. 2b, each of the rectangular shapes are spaced from the remaining shapes in a particular grid pattern. In FIG. 2c each shape is contiguous with the next adjacent shape at the corners thereof.

It will occur to those skilled in the laminating art that other patterns may be provided in accordance with the present invention utilizing straight lines, dots, wavy lines, assorted shapes, or any combination which, when distorted by fusion or flow of the laminate material, is readily detected. An example of the wide variety of patterns useable in a process in accordance with the present invention is illustrated in a Catalog of Graphic Arts Transfer Patterns published by the Prestype Corporation of Carlstadt, N.J., copyright 1972. On pages 70 and 71 of the catalog are numerous patterns in a variety of arrangements. What is essential is that the resolution of the pattern be sufficiently fine to detect a minimum flow of adhesive which resolution will distinguish the border-line situation between an acceptable bond and an unacceptable bond. This resolution is one in which a minimum pattern distortion is readily detected utilizing a particular inspection technique, e.g., waves of electromagnetic energy in a given frequency, i.e., X-ray. With X-rays, high mass particles remain opaque while low mass material remains relatively transparent.

By pattern distortion is meant a bleeding or flow of the pattern at the edges thereof or a change in the geometry of the pattern. Thus, not only is the shape of the pattern components, i.e., dots, lines squares and so forth, and the pattern symmetry or regularity significant, but also the number of contrasting edges present in a given area.

Figure 4A:
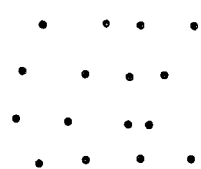
Figure 4B:
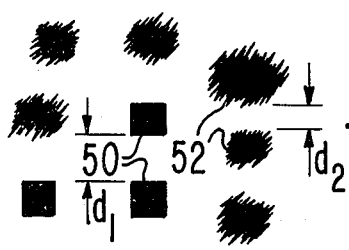

The distortion of the pattern component edges resulting from the flow of the adhesive layer causes a change in pattern edge sharpness, i.e., bleeding. The edges of the pattern components; e.g. lines, dots; deviate from a sharply contrasted demarcation and become fuzzy, flowing or otherwise show a clear deviation from a sharp, crisp edge. See FIG. 4b, wherein the original pattern component is a solid square configuration as shown at 50. After flow of the pattern laminate material, i.e., the adhesive 16, FIG. 1, the edges of the square bleed or flow as shown at 52. In FIG. 4a, distortion of the geometry of an originally symmetrical grid pattern of dots is shown. In this instance, the dots are no longer in a regular grid. In FIG. 4b geometric distortion is illustrated by the difference in spacing $d_1$ in the undistorted pattern at 50 and spacing $d_2$ in the distorted pattern at 52.

The bleeding distortion provides the sharper resolution. The sharper the edge definition, the greater the resolution of the pattern, the more accurate the examination. This sharp edge definition is provided, for example, by a fine dot pattern as occurs in a lithographic printing. Any flow of the dot pattern base material tends to reduce the contrast consistency. The dot pattern provides maximum coverage of an area to be inspected.

It is to be understood that the material forming the pattern should not change detection characteristics during storage time. The pattern material should not diffuse into the carrier material or disburse in a way such that the pattern material becomes invisible while the fusing or bonding process is in progress or at any time thereafter except as a direct result of the flow of the pattern carrier material. That is, the pattern material should not disperse or change characteristics when actual fusing does not occur in the carrier material. The pattern material should be chemically inert to the laminate material adhesive, solvent and environment at storage and seal temperatures. For these reasons barium sulfate dust is preferred. Further, the pattern material should cover no more than about 10% of the lamination area to prevent interference with the adhesive action.

In addition, the pattern material should be made of a material that is readily detected upon suitable examination with visual, X-ray or any other suitable optical or electromagnetic detection techniques. Barium sulfate provides the desired opaqueness in an X-ray detection process.

Where the pattern material is a liquid solution such as a dust dispersed in a liquid carrier comprising the adhesive solvent, the solution may be rolled, sprayed, brush stenciled or otherwise applied in a suitable manner onto the fusible adhesive 16. While the exemplary sprayed process is illustrated in FIG. 3, it is to be understood that the other processes, especially the roller type, are equally satisfactory.

Figure 3:
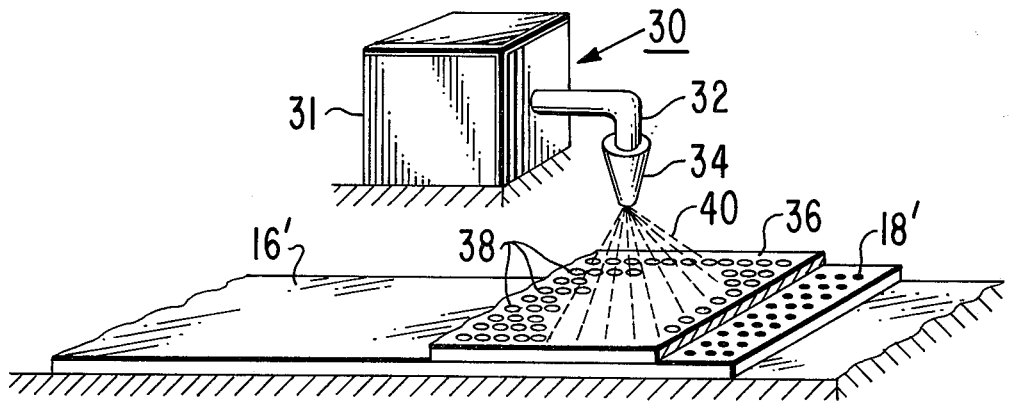

In FIG. 3 a suitable apparatus 30 is provided for spraying barium sulfate dust particles in a solution of chlorinated aliphatic ketone solvent in the proportion of 10% dust to solvent by weight comprising 1, 1, 2 trichloroethane. Powders of barium sulfate are commerically available in particle size in the order of one micron. It is to be understood that this particle size is exemplary, and other sizes may be used in accordance with a given set of conditions in a particular application. The particle size should be that size that permits a diffusion or bleeding of the pattern component, i.e., dot, line, when fusion occurs. Where geometric distortion is of primary significance then, of course, the particle size may be secondary.

Apparatus 30 includes a pressurized container 31, a suitable hose 32 and spray nozzle 34. Valves, controls, pressure pumps (not shown) are conventional and may be of the type used in a conventional paint spray apparatus or the like. Nozzle 34 is positioned adjacent stencil 36.

Stencil 36 is an elongated sheet having a plurality of apertures 38 arranged in a suitable pattern of the type shown in FIG. 2a. Stencil 36 extends the complete length of adhesive 16'. Stencil 36 is placed contiguous with one surface of adhesive 16' in a manner similar to the well known silk screen process. With the stencil 36 thus positioned, nozzle 34 is directed in a manner to spray the suspended barium sulfate dust solution 40 through the apertures 38 in a thin and uniform coating.

The coating is made sufficiently heavy to saturate each aperture 38 with the solution, wetting the adhesive at each aperture. The solution is then permitted to dry either in the air or by suitable blower means (not shown). At this time the stencil is removed leaving a grid pattern of barium sulfate dust particles on the adhesive. The carrier liquid for the dust particles being a solvent for the adhesive softens the adhesive an amount sufficient for the dust particles to become adhered to the adhesive. Upon evaporation of the solvent carrier liquid, the dust particles are securely cemented to the adhesive 16'.

The adhesive with the grid pattern thereon is disposed between two layers of material to be laminated as explained above with respect to FIG. 1. Heat and pressure are applied to the extent necessary to cause adhesive 16' to flow as known in the pressure sealing art. After cooling, the assembly is X-rayed at a suitable voltage and the X-ray film examined for pattern distortion. The lower the voltage, the higher the contrast. If a pattern distortion is present throughout the laminated area, then the adhesive flowed. If any of the original pattern components are present undistorted, then a poor joint is indicated at that area.

Where the materials to be bonded are fabrics of the type coated with a thermoplastic material or other suitable fusible material, then the pattern material may be deposited directly on one of these layers.

It should be appreciated that the type of pattern, e.g., lines, rectangles, circles, dots and so forth may be determined by the type of material to be bonded. Coarse, rough, grainy material would be suitable with a line type of pattern, whereas a smooth, slick, surface would be best with a fine dot pattern.

Regardless of which pattern or degree of resolution utilized, it is essential that the resolution be of at least the same order as the expected variation flow of the adhesive carrier material. That is, if a one mil flow of adhesive would be sufficient to provide a good bond, then the pattern edge sharpness and pattern material, i.e., dust, should be fine enough to provide an easily identifiable pattern edge distortion in the presence of a one mil flow of the fused material. Preferably, in this instance, the pattern distortion should result with a tenth mil flow to provide a tenfold amplification factor. Also to be taken into consideration is the resolution of the particular photographic optics or other detection process utilized. The resolution of the detection process should be sufficiently great so as to permit an operator to distinguish between a distorted and non-distorted pattern attributed directly to the presence or absence of fusion of the corresponding carrier material.

What is claimed is:

1. A method of detecting the adherence of a first member to a second member between which is disposed a layer of adhesive, said adhesive tending to bond said members together only when said adhesive is caused to change from a solid state to a liquid state, said method comprising:
   depositing a material in a given pattern on said adhesive when in the solid state,
   disposing said solid adhesive between said members,
   causing said adhesive to change from a solid state to a liquid state when disposed between said members, the change in state of said adhesive disturbing said given pattern, and
   examining said material for the presence of said given pattern.

2. The method of claim 1 wherein said members are transparent to electromagnetic radiation and said material is opaque to electromagnetic radiation, said examining step including the step of X-raying said members and said disposed adhesive.

3. The method of claim 1 wherein said depositing step includes depositing particles suspended in a solvent of said adhesive.

4. The method of claim 1 wherein said depositing step includes the step of forming said pattern of a plurality of dots.

5. The method of claim 1 wherein said depositing step includes the step of forming said pattern of a plurality of lines.

6. The method of claim 1 wherein said depositing step includes forming said pattern with sharp edges.

7. A method of detecting the adherence of a first layer to a second layer between which layers is disposed a layer of adhesive, said adhesive tending to bond said layers together only when said adhesive is caused to change from a solid state to a liquid state in response to heat and pressure applied thereto, said method comprising:
   depositing a particulate material in a given pattern on said adhesive layer when in the solid state,
   applying heat and pressure to said layers to change said disposed adhesive from a solid state to a liquid state, the change of state of said adhesive causing a discernable pattern distortion in that deposited material contiguous with the changed adhesive, and
   inspecting said layers for the presence of said distortion.

8. A process for the non-destructive inspection of a bonded laminated article comprising:
   depositing a material in a given pattern on a first portion of said article, said first portion to be bonded to a second portion of said article,
   placing said portions contiguous with each other with said deposited material disposed at the interface therebetween,
   bonding said first portion to said second portion in a manner to distort said pattern only when a bond is present at said interface, and
   examining said interface for the presence of said distorted pattern.

9. A process for the non-destructive inspection of a bonded laminated article, comprising:
   depositing a material in a given pattern in the interface between the portions of said article to be laminated,
   bonding said portions together at said interface in a manner to distort discernably said pattern only when a bond is produced, and inspecting said bonded portions for the presence of a distorted pattern.

10. A process for the non-destructive inspection of a laminated article comprising:
depositing a material in a predetermined pattern on one layer in the interface between first and second layers of said article,
bonding said layers together by fusing said one layer at said interface, said fusing tending to distort said pattern, and
inspecting said fused layer for the presence of said distorted pattern.

* * * * *